(12) United States Patent
Bear et al.

(10) Patent No.: US 11,517,506 B2
(45) Date of Patent: *Dec. 6, 2022

(54) SYSTEM AND METHOD FOR TRACKING AND REGULATING REMOVAL OF PATIENT MEDICATIONS

(71) Applicant: Medication Adherence Technologies, LLC, Dover, DE (US)

(72) Inventors: David Bear, Wellesley, MA (US); Jay Carlson, Lincoln, NV (US); Charles Lee, Omaha, NE (US)

(73) Assignee: Medication Adherence Technologies, LLC, Dover, DE (US)

( * ) Notice: Subject to any disclaimer, the term of this patent is extended or adjusted under 35 U.S.C. 154(b) by 6 days.

This patent is subject to a terminal disclaimer.

(21) Appl. No.: 17/165,417

(22) Filed: Feb. 2, 2021

(65) Prior Publication Data

US 2021/0154101 A1 May 27, 2021

Related U.S. Application Data

(63) Continuation of application No. 16/845,901, filed on Apr. 10, 2020, now Pat. No. 10,918,576.

(Continued)

(51) Int. Cl.
*A61J 7/04* (2006.01)
*A61J 7/00* (2006.01)
(Continued)

(52) U.S. Cl.
CPC ............. *A61J 7/0427* (2015.05); *A61J 1/03* (2013.01); *A61J 7/0076* (2013.01); *G16H 20/13* (2018.01); *G16H 40/67* (2018.01)

(58) Field of Classification Search
CPC ... G07F 17/0092; G07F 11/66; G07F 11/1168
See application file for complete search history.

(56) References Cited

U.S. PATENT DOCUMENTS

| 1,820,341 A | 8/1931 | Beeson |
| 3,964,638 A | 6/1976 | Dimauro |

(Continued)

FOREIGN PATENT DOCUMENTS

WO  WO-2005/023171  3/2005

OTHER PUBLICATIONS

Non-Final Office Action from U.S. Appl. No. 16/845,901, dated Apr. 10, 2020.

(Continued)

*Primary Examiner* — Timothy R Waggoner
(74) *Attorney, Agent, or Firm* — Morse, Barnes-Brown & Pendleton, P.C.; Sean D. Detweiler, Esq.; James M. McKenzie, Esq.

(57) ABSTRACT

A pill packet dosage tracking and gating device is provided. The device includes a container, a gate, and a controller. The container includes a reservoir configured to hold a stream of pill packets and an extraction channel configured to guide the passage of the stream of pill packets from the reservoir out of the container. The gate is disposed in the extraction channel and is configured to vertically transition from a closed position blocking extraction of a pill packet of the stream of pill packets and an open position allowing extraction of a pill packet. The controller is configured to monitor the extraction of pill packets and control the transition of the gate from the closed position to the open position.

19 Claims, 12 Drawing Sheets

Related U.S. Application Data

(60) Provisional application No. 62/832,089, filed on Apr. 10, 2019.

(51) Int. Cl.
  *G16H 20/13* (2018.01)
  *G16H 40/67* (2018.01)
  *A61J 1/03* (2006.01)

(56) References Cited

U.S. PATENT DOCUMENTS

| | | |
|---|---|---|
| 5,230,441 A | 7/1993 | Kaufman et al. |
| 5,335,816 A | 8/1994 | Kaufman et al. |
| 5,630,347 A | 5/1997 | Elvio |
| 6,394,306 B1 * | 5/2002 | Pawlo ............... B65D 83/0463 221/258 |
| 7,264,136 B2 | 9/2007 | Willoughby et al. |
| 7,857,163 B2 | 12/2010 | Shigeyama et al. |
| 8,074,426 B2 | 12/2011 | Luciano, Jr. et al. |
| 8,196,774 B1 | 6/2012 | Clarke et al. |
| 8,924,227 B2 | 12/2014 | Fellows et al. |
| 9,355,222 B2 | 5/2016 | Chudy et al. |
| 9,361,431 B2 | 6/2016 | Fauci |
| 9,504,629 B2 | 11/2016 | Blomquist et al. |
| 9,846,766 B2 * | 12/2017 | Apell ................. G07F 17/0092 |
| 10,032,005 B2 | 7/2018 | Fauci |
| 10,045,914 B2 | 8/2018 | Yuyama et al. |
| 10,176,663 B2 | 1/2019 | King et al. |
| 10,180,018 B1 | 1/2019 | Simpson et al. |
| 10,918,576 B2 * | 2/2021 | Bear ...................... G16H 40/67 |
| 2009/0250481 A1 | 10/2009 | Campanini |
| 2011/0232435 A1 | 9/2011 | Jaynes |
| 2012/0081225 A1 * | 4/2012 | Waugh .................. G16H 40/67 340/540 |
| 2012/0083666 A1 | 4/2012 | Waugh et al. |
| 2012/0166215 A1 | 6/2012 | Choi et al. |
| 2014/0114471 A1 * | 4/2014 | Kim ...................... G16H 20/13 221/30 |
| 2016/0324727 A1 | 11/2016 | Waugh et al. |
| 2016/0355322 A1 | 12/2016 | Burton, Jr. et al. |
| 2016/0374902 A1 | 12/2016 | Govindasamy et al. |
| 2019/0103000 A1 * | 4/2019 | Jones .................... G07D 11/60 |

OTHER PUBLICATIONS

International Search Report from International Application No. PCT/US2020/027726; dated Jun. 23, 2020.

Non-Final Office Action from U.S. Appl. No. 16/845,901; dated Jul. 27, 2020.

Notice of Allowance from U.S. Appl. No. 16/845,901; dated Oct. 29, 2020.

* cited by examiner

SYSTEM AND METHOD FOR TRACKING AND REGULATING REMOVAL OF PATIENT MEDICATIONS

CROSS-REFERENCE TO RELATED APPLICATION(S)

This application is a continuation of co-pending U.S. application Ser. No. 16/845,901, filed Apr. 10, 2020, which claims priority to, and the benefit of, U.S. Provisional Application No. 62/832,089 filed Apr. 10, 2019 for all subject matter contained in said application. The disclosures of said patent applications are hereby incorporated herein by reference in their entirety.

FIELD OF THE INVENTION

The present invention relates to tracking and control of complex medication regimens and/or safe removal of medications with serious side effects, abuse or diversion potential suitable for use in patients' homes, nursing homes, or Assisted Living Facilities. Use of the invention facilitates increased medication adherence, monitoring of side effects, and enables use of specialized medications outside costly hospital settings or doctors' offices. In particular, the present invention provides a solution for a low cost, controlled, and monitored administration of pills and capsules.

BACKGROUND

Patients prescribed more than five separate medications have an average adherence to prescribed dosage and frequency of only 40%. Currently, more than 25 million Americans fall into this category, including those with costly chronic illnesses such as heart failure, cancer on chemotherapy, organ transplantation requiring immunosuppression, mood disorders, and multi-illness co-morbidities. Based on aging demographics, this number is estimated to rise to 40 million by 2025.

Failure to take medications as prescribed within a complex regimen leads to deterioration in health, visits to emergency rooms, and preventable hospitalizations.

Furthermore, there is an epidemic of opioid abuse in the US, conservatively estimated to add 70B in cost to the healthcare system, creating incalculable suffering and death. Other medications subject to abuse are psychostimulants used to treat attention deficit hyperactivity disorder (ADHD), vigilance enhancers for severe sleep disorders, and benzodiazepine anxiolytics.

Packaging drugs for convenience in the form of a linear roll of pouches, blisters or sachets has been in use in many European countries for more than ten years. More recently in the US, a large mail-order pharmacy has coupled automated loading and inspection of sachets or packets holding multiple tablets and capsules with distribution of a linear spool of time labeled doses within a cardboard, passive, container (e.g., PillPack®). Similar packing technology is utilized by ExactCare® and CVS Caremark™.

While packaging multiple medications in sachets, packets or pouches for dosing limits the need for the patient to deal with a plethora of bottles or vials containing single medications, the task of manually pulling a varying number of packets or pouches to achieve, for example, doses of greater than 15 pills at some time points, presents a daunting task for patients on complex regimens. This is especially the case for patients with mild cognitive impairment, a diagnosis with increased prevalence among the elderly.

Furthermore, in the absence of monitoring, patients can omit doses or, by pulling the wrong number of pouches, take the following series of time sensitive pills at inappropriate times, creating propagating errors in adherence.

Moreover, in the absence of a security system, distributing medications such as opioids in a roll of sachets does not prevent overuse by the patient, illicit diversion, or theft of significant quantities of abusable drugs.

SUMMARY

There is a need for systems and methods to raise adherence among these complex patients, greatly improving their quality of care while substantially reducing its cost. The present invention addresses these needs, in addition to other improvements and patentable characteristics. Unlike conventional devices and systems, the present invention does not require specialized labeling or barcoding initiated by a particular pharmacy system. The system has no motor-powered mechanisms for pushing or advancing dose units, thereby reducing failure modes, increasing reliability, and reducing cost.

As such, the present invention provides a low-cost accessory, usable with a broad array of pill packets such as linear strips of pouches, packets, sachets, or blisters, which addresses both of the problems above, thereby simultaneously addressing the need to safely administer these medications, reduce abuse which often leads to addiction, and deter illicit diversion of medication.

In accordance with embodiments of the present invention, a pill packet dosage tracking and control device is provided. The device includes a container, a gate, and a controller. The container includes a reservoir configured to hold a stream of pill packets and an extraction channel configured to guide the passage of the stream of pill packets from the reservoir out of the container. The gate is disposed in the extraction channel and is configured to vertically transition from a closed position blocking extraction of a pill packet of the stream of pill packets and an open position allowing extraction of a pill packet. The controller is configured to monitor the extraction of pill packets and control the transition of the gate from the closed position to the open position.

In accordance with aspects of the present invention, the stream of pill packets comprises one or more packet containing a predetermined dosage of pills wherein each pill packet is detachably connected to the next pill packet in the stream. In certain aspects, the stream of pill packets is provided in a roll for easy loading into the reservoir of the container to be extracted—through the extraction channel.

In accordance with aspects of the present invention, the container further comprises an upper shell and a lower shell wherein removing the upper shell provides access to the reservoir and extraction channel.

In accordance with aspects of the present invention, the gate includes an inner slider, and outer slider, an electric motor, and a linkage. The outer slider is slidably coupled to the inner slider and has an engagement edge for engaging the stream of pill packs. The motor is used to position the gate but not advance pouches. The linkage connects the motor to the inner slider and converts the rotational movement of the motor to the linear movement of the gate. In certain aspects, the gate is mechanically biased in a closed position by springs between the inner slider and outer slider. In some aspects, the gate further includes a receiver configured to receive the engagement edge of the outer slider when the gate in a closed position. In still other aspects, the engagement edge of the outer slider has an asymmetrical shape such as a guillotine blade configuration.

In accordance with aspects of the present invention, the extracting of pill packets through the extraction channel causes the gate to transition from a closed position to an open position indicating to the controller that a pill pouch has been extracted.

In accordance with aspects of the present invention, the controller is configured to maintain a count of pill packet extracted from device. In other aspects, the controller is configured to detect the extraction of one or more pill packets corresponding to a timed dosage and lock the gate in a closed position until the next timed dosage.

In accordance with aspects of the present invention, the controller includes a processor and one or more sensors. The processor is configured to monitor and control the gate and thus the extraction of pill packets. The one or more sensors are configured to detect the position of the gate. In certain aspects the controller also includes wireless connectivity. In some such aspects, the wireless connectivity can be used to control the device remotely.

In accordance with aspects of the present invention, the device further includes a display mounted on the container providing the status of the device. In some such aspects, the display is a touch screen display.

In accordance with aspects of the present invention, the device further includes a sensor disposed along the extraction channel configured to detect a pill packet. In some aspects, the sensor is an optical scanner. In other aspects, the sensor is a camera.

In accordance with aspects of the present invention, the device may be in communication with an authorization device that indicates to the controller whether a pill pouch can be extracted.

BRIEF DESCRIPTION OF THE FIGURES

These and other characteristics of the present invention will be more fully understood by reference to the following detailed description in conjunction with the attached drawings, in which.

DETAILED DESCRIPTION

Figure 1:
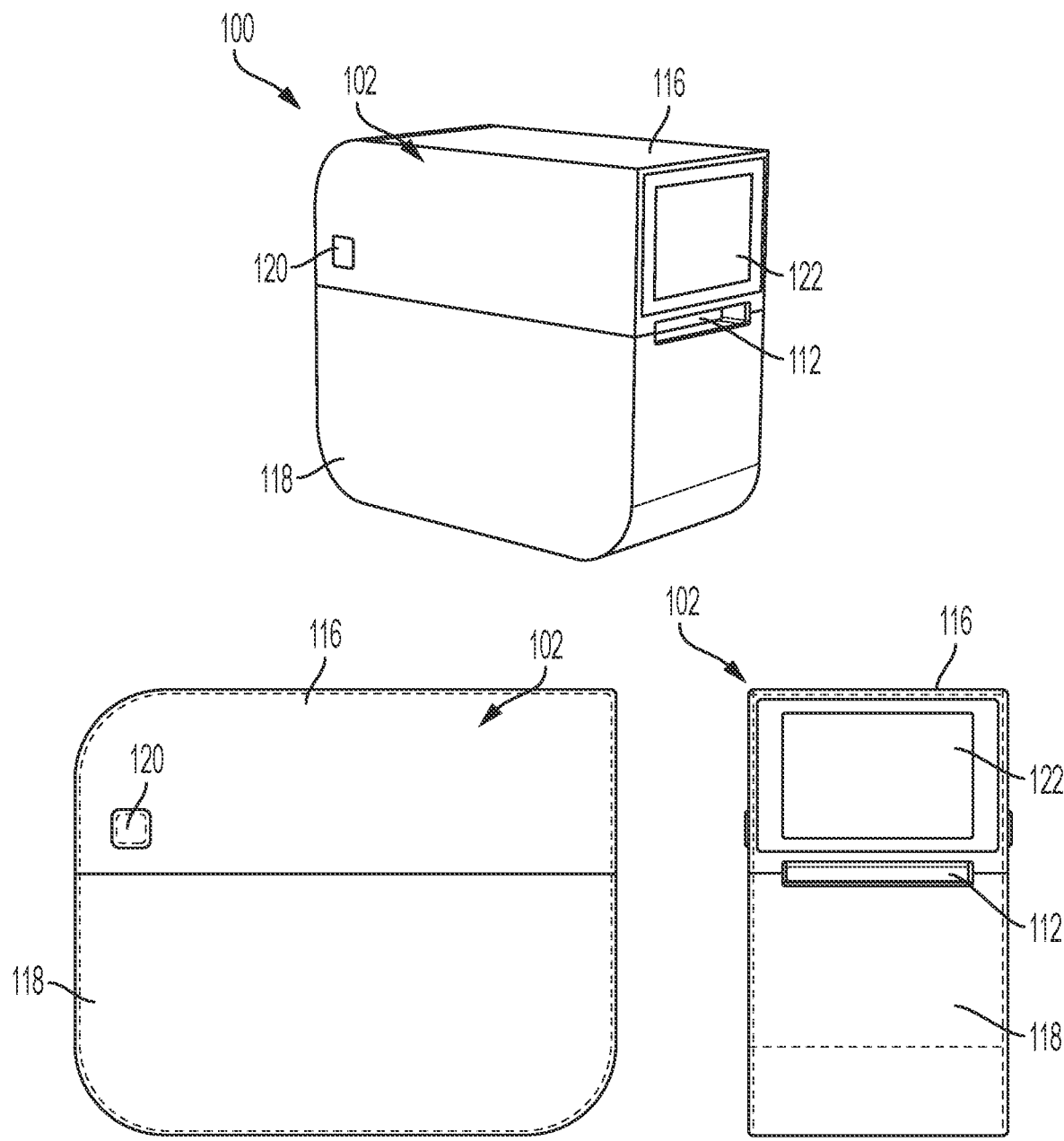
FIG. 1 depicts a perspective view, a side view, and a front view of the pill packet dosage tracking device in accordance with embodiments of the present invention.

An illustrative embodiment of the present invention relates to a system and method for tracking of patient medication removal.

FIG. 1 through FIG. 12 are diagrammatic illustrations of an embodiment of the present invention in the form of an accessory to a stream of packets, pouches, or sachets (such as those packets, pouches, or sachets prepared by Parata Pharmacy Robotics and distributed by PillPack, Inc. or ExactCare Pharmacy). The invention includes a container into which the pill packet stream is loaded. The patient actively participates in dosing by pulling the pill packets through a gate.

In terms of behavioral psychology first established by B. F. Skinner, the patient's removal of pouches following a reminding signal constitutes Operant Behavior, subject to increased frequency by a reinforcer. This distinguishes the device from motorized dispensers which do not rely on the patient emitting a response.

The pill packet stream can move freely or be braked under mechanized control to indicate to the patient that they have withdrawn their full dose of packets at the appropriate time. An indicator can be displayed on the device or auditory instructions from this or another device such as a home voice assistant may aid the patient. The gate operates in response to a signal from a controller embedded in the device, or from an external device such as, a smart phone, tablet, or computer capable of Internet connectivity, and/or biometric verification or transmission of its GPS coordinates.

FIG. 1 through FIG. 12, wherein like parts are designated by like reference numerals throughout, illustrate an example embodiment or embodiments of a system and method for tracking of pill pack medications, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed, such as the size, shape, or type of elements or materials, in a manner still in keeping with the spirit and scope of the present invention.

The system of the present invention can utilize data describing the time of dosing of the patient's regimen, from which the number of pouches required at each dose time is readily determined. These data could be supplied by the dispensing pharmacy, kept in a Health Insurance Portability and Accountability Act (HIPAA) secure format for access over the world wide web or Internet, or provided on the packaging of the stream of pill packets or the pill packets themselves. Once obtained the data can be stored locally on the device.

As shown in FIGS. 1 through 11, a pill packet dosage tracking device 100 is provided. The device includes a container 102, a gate 104, and a controller 106. The container includes a reservoir 108 configured to hold a stream of pill packets 110 and an extraction channel 112 configured to guide the passage of the stream of pill packets 110 from the reservoir 108 out of the container 102. The gate 104 is disposed in the extraction channel 112 and is configured to vertically transition from a closed position blocking extraction of a pill packet 114 of the stream of pill packets 110 and an open position allowing extraction of a pill packet 114. The controller 106 is configured to monitor the extraction of pill packets 114 and control the transition of the gate 104 from the closed position to the open position.

FIG. 1 provides a perspective view, a side view, and a front view of the container 102 providing an example of the dimensions for the container 102 of the device 100. The extraction channel 112 can also be seen in the front face of the container 102. In this example, the container 102 is formed of an upper shell 116 and a lower shell 118. The upper shell 116 can be separated from the lower shell through the use of a shell latch release 120. The container 102 is sized and dimensioned to be placed on a table or countertop to be easily accessible by a user. In certain embodiments, the container 102 is approximately 7 inches tall, 4 inches wide and 8.5 inches deep, but other dimensions of similar magnitude to enable countertop placement are considered within the scope of the present invention. The container 102 may be formed of plastic, metal, or other suitable material as well as any combination thereof. In certain embodiments, such as seen here, a display 122 may also be provided on the container 102 of the device 100. The display will be discussed in more detail below. Other sizes and configuration will be apparent to one skilled in the art given the benefit of this disclosure.

Figure 2:
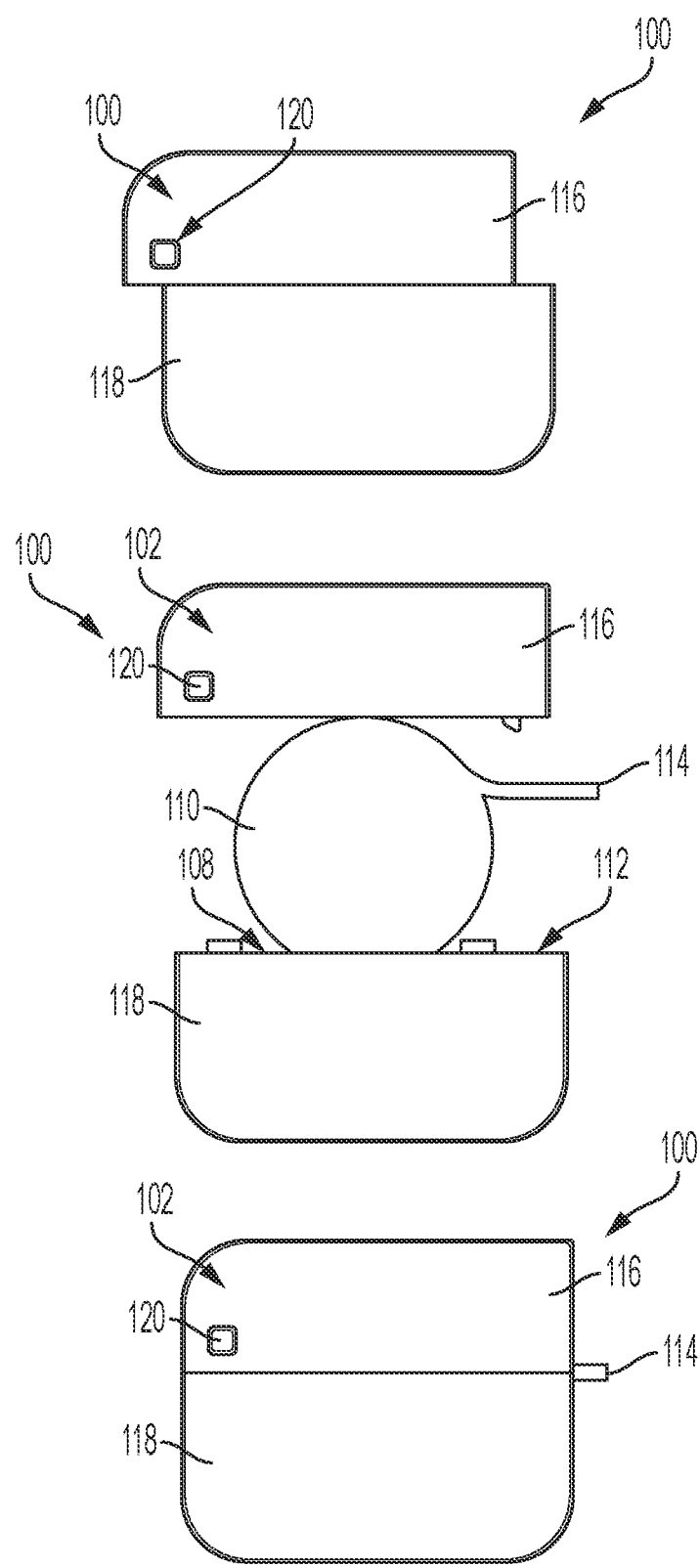
FIG. 2 depicts the loading of a stream of pill packets into the pill packet dosage tracking device in accordance with embodiments of the present invention.

FIG. 2 depicts the process of loading a stream of pill packets 110 into the device 100. The upper shell 116 is separated from the lower shell 118 by pressing the latch release 120 and sliding the upper shell 116 back in relation to the lower shell 118. Once disengaged the upper shell 116 can be removed providing access to the reservoir 108 in the container 102. The stream of pill packets 110, here provided as a roll, can be loaded into the reservoir 108 and extraction channel 112, such that portion of a pill packet 114 extend out from container 102 thru the extraction channel 112. Once the stream of pill packets 110 is loaded, the upper shell 116 can be reattached to the lower shell 118 and the device 100 is ready for operation. In operation, pill packets 114 are extracted pulling on the portion of packet 114 extending from container 102. When pulled, the pill packet 114, which is detachably connected to the next pill packet in the stream of pill packets 110, pulls the stream of pill packets 110 from the reservoir 108, thru the extraction channel 112, and out of the container 102 allowing the next pill packet 114 in the stream of pill packets 110 to be available for extraction.

Figure 3:
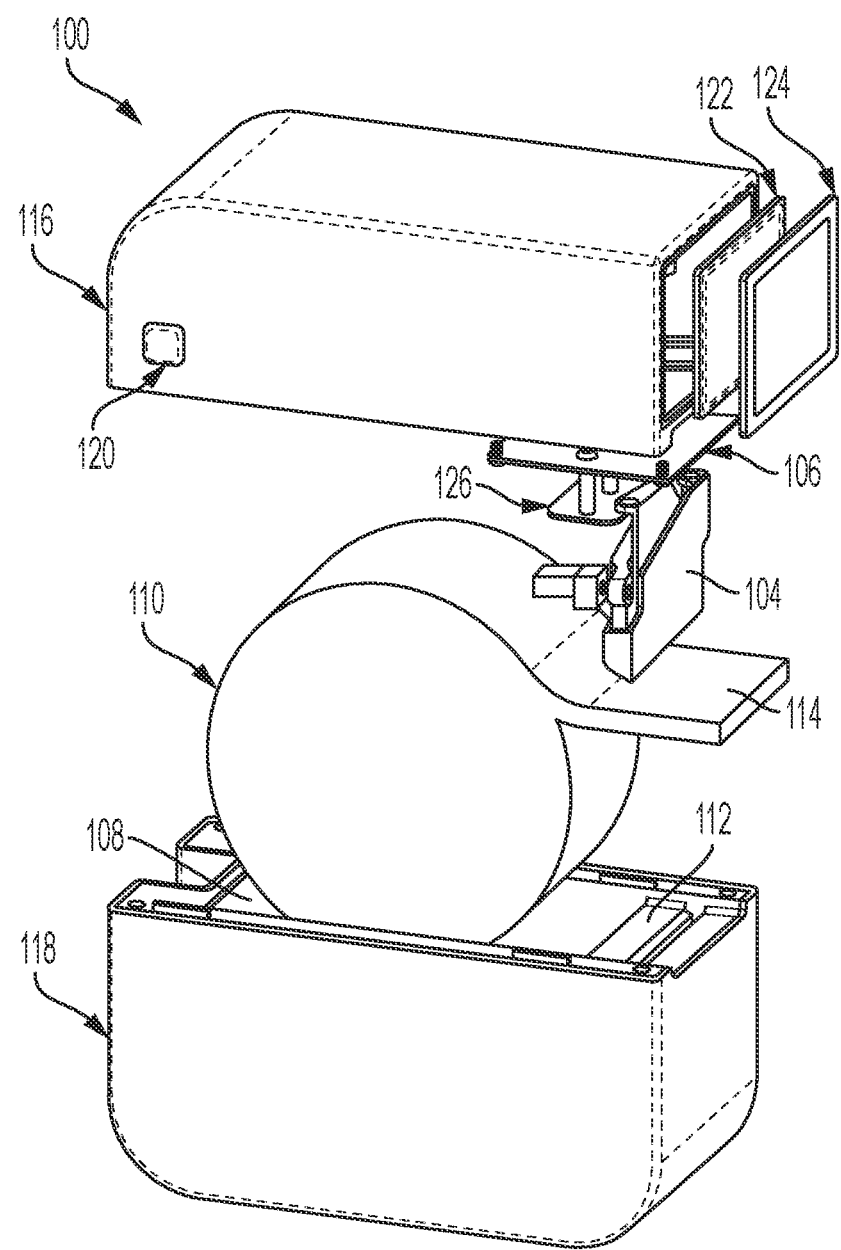
FIG. 3 is an exploded perspective view of the pill packet dosage tracking device in accordance with embodiments of the present invention.

FIG. 3 provides an exploded view of the pill packet dosage tracking device 100. Illustrated are upper 116 and lower 118 shells of the container 102 which encapsulates the stream of pill packets 110 loaded in the reservoir 108 and extraction channel 112 as well as the gate 104 and controller 106. In this embodiment the display 122 is a Liquid Crystal Display (LCD) which has touch capability provided by a capacitive touch panel touch screen 124 placed over the LCD display 122. In other embodiments, controls such as buttons or switches may be provided instead of touch screen capability. In certain embodiments, the device 100 may also be provided with a sensor 126, such as an optical sensor or camera, for monitoring packets 114 as the pass thru the extraction channel 112. These elements will be discussed in more detail below.

Figure 4:
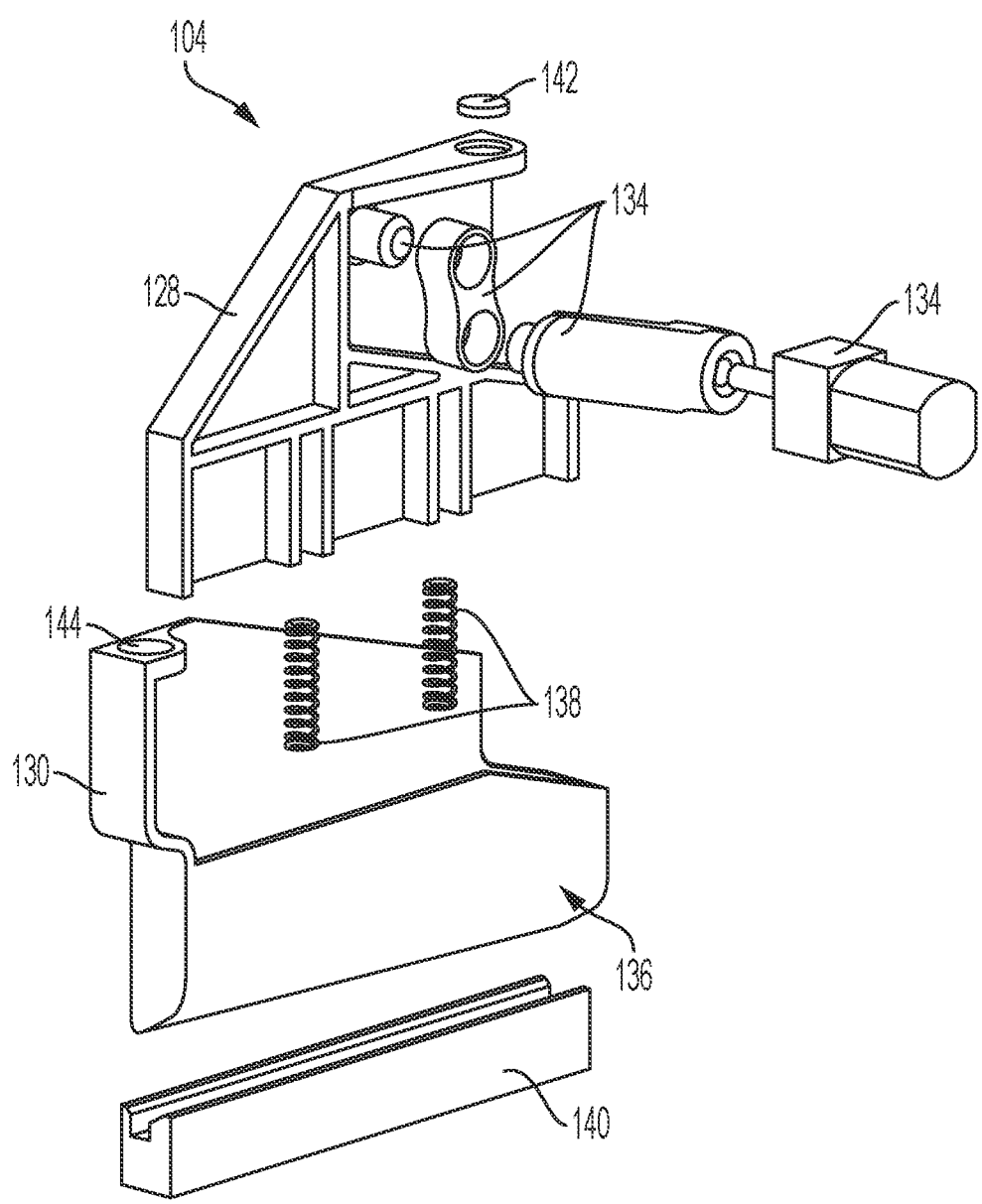
FIG. 4 is an exploded perspective view of the gate of pill packet dosage tracking device in accordance with embodiments of the present invention.

In the example of FIG. 3, the gate 104 can be seen extending across the extraction channel 112 configured to move vertically to engage the pill packets 114 of the stream of pill packets 110. FIG. 4 provides an exploded view where all the elements of the gate 104 can be seen. These elements include an inner slider 128, an outer slider 130, a motor 132 and a linkage 134. The outer slider 130 is slidably coupled to the inner slider 128 and has an engagement edge 136 for engaging the pill packets 114 of the stream of pill packets 110. The motor 132 is used to position the gate 104, not to advance or control the advance of the stream of pill packets 110. The linkage 134 connects the motor 132 to the inner slider 128 and converts the rotational movement of the motor 132 to the linear vertical movement of the gate 104. The inner slider 128, outer slider 130, and linkage 134 may be formed of plastic, metal, or other suitable material as well as any combination thereof.

In certain embodiments, the gate 104 is mechanically biased in a closed position by springs 138 between the inner slider 128 and outer slider 130. In some embodiments, the gate 104 further includes a receiver 140 configured to receive the engagement edge 136 of outer slider 130 when the gate 104 is in a closed position. The receiver 140 can be formed of plastic, metal or other suitable material as well as any combination thereof. In still other aspects, the engagement edge 136 of the outer slider 130 has an asymmetrical shape such as a guillotine blade configuration optimized for the tearing properties of the pouch stream.

In some embodiments, the inner slider 128 as well as the outer slider 130 are provided with magnets 142, 144 or other indicators that can be used in conjunction with sensors of the controller 106 to detect the position of the inner slider 128 and outer slider 130. Magnet 142 is used to determine the position of the inner slider 128 and magnet 144 on the outer slider 130 is used to determine the position of the outer slider 130.

Figure 5:
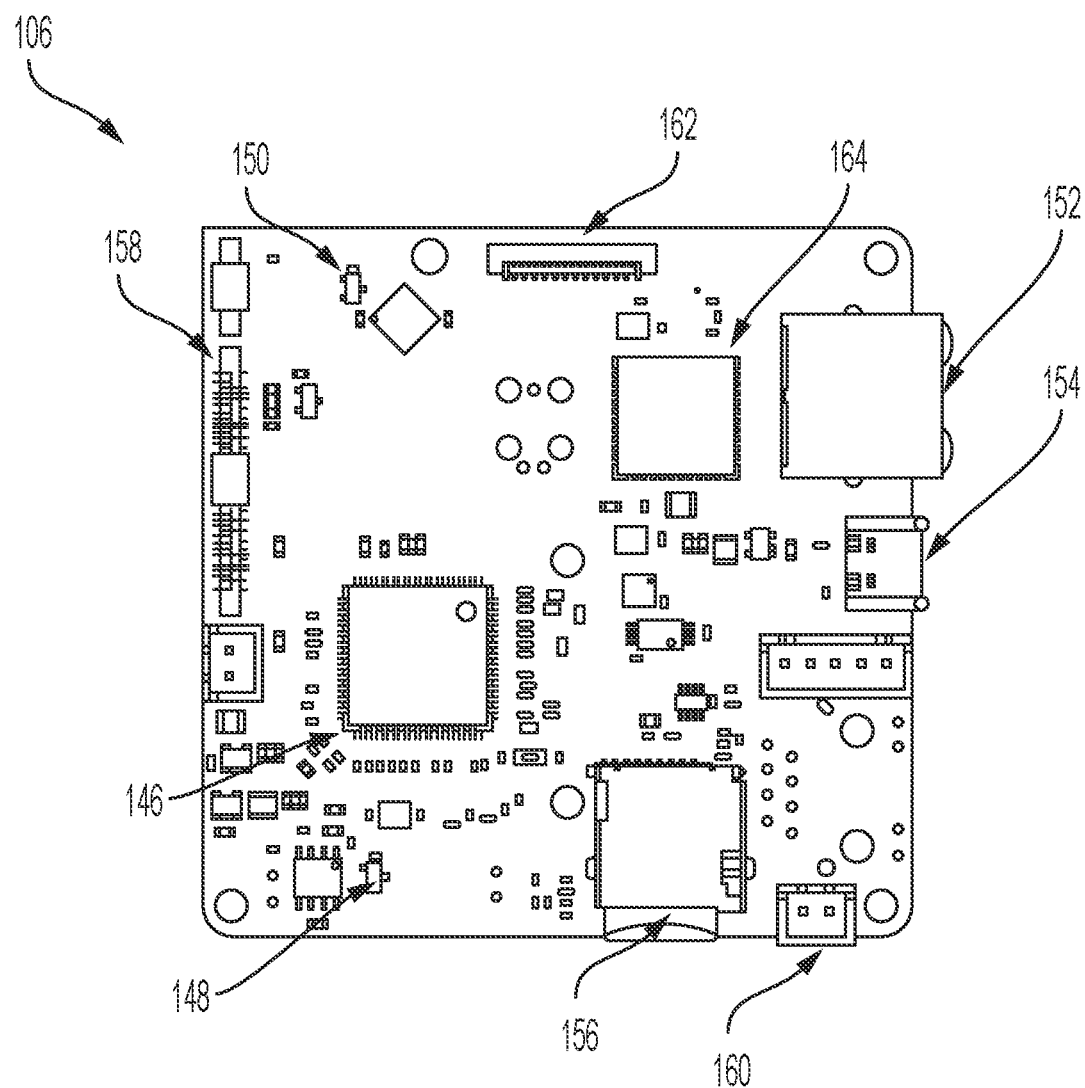
FIG. 5 depicts a controller of the pill packet dosage tracking device in accordance with embodiments of the present invention.

The motor 132 is also controlled and monitored by the controller 106. FIG. 5 depicts one embodiment of controller 106 that can be used in conjunction with the device 100. The controller 106 of FIG. 5 is a printed circuit board (PCB) configured, sized and dimensions to be placed above the gate 104. In certain embodiments, the printed circuit board is approximately 3 inches by 3 inches square. The controller 106 includes a processor 146 and one or more sensors 148, 150. The processor 146 is configured to monitor and control the gate 104 and thus the extraction of pill packets 114. In some embodiments, the processor 146 keeps track of the amount and time of pill extraction. In some such embodiments, the processor 146 of the controller 106 is responsible for allowing or preventing the extraction of a pill packet based on the time of day, or amount of pill packets required to fulfill a dosage. In such embodiments, the processor 146 may receive and store prescription information regarding the type and/or number of pills being administered by the device 100 and control extraction accordingly.

The one or more sensors 148, 150, in this case Hall-Effect sensors, are configured to detect the position of the gate. A Hall-Effect sensor 148 is configured to detect the magnet 142 on the inner slider 128 to, in conjunction with the processor 146, determine the position of the inner slider 128. The Hall-Effect sensor 150 is configured to detect the magnet 144 on the outer slider 130 to, in conjunction with the processor 146, determine the position of the outer slider 130. Other possible sensor and configurations will be apparent to one skilled in the art.

The controller 106 of FIG. 5 is also provided with a number of ports including an ethernet jack 152, Universal Serial Bus (USB) port 154, and SD card slot 156 that can be used to provide data to and from the processor 146. In some embodiments the controller 106 may also include wireless connectivity such as Bluetooth®, cellular, Wi-Fi®, Radio Frequency Identification (RFID), or any combination thereof of wireless communication protocols and technologies. The controller 106 also includes several connectors for connecting the processor 146 to other devices. The connectors include display connector 158 for driving the display 122 of the device, and in embodiments with touch screen capability, receiving inputs from the touch screen 124; a motor connecter 160 for controlling the motor 132; and a sensor connector 162 for connecting an optical sensor or camera. In certain embodiments a secondary processor 164 can be provided to add additional functionality or processing.

Figure 6:
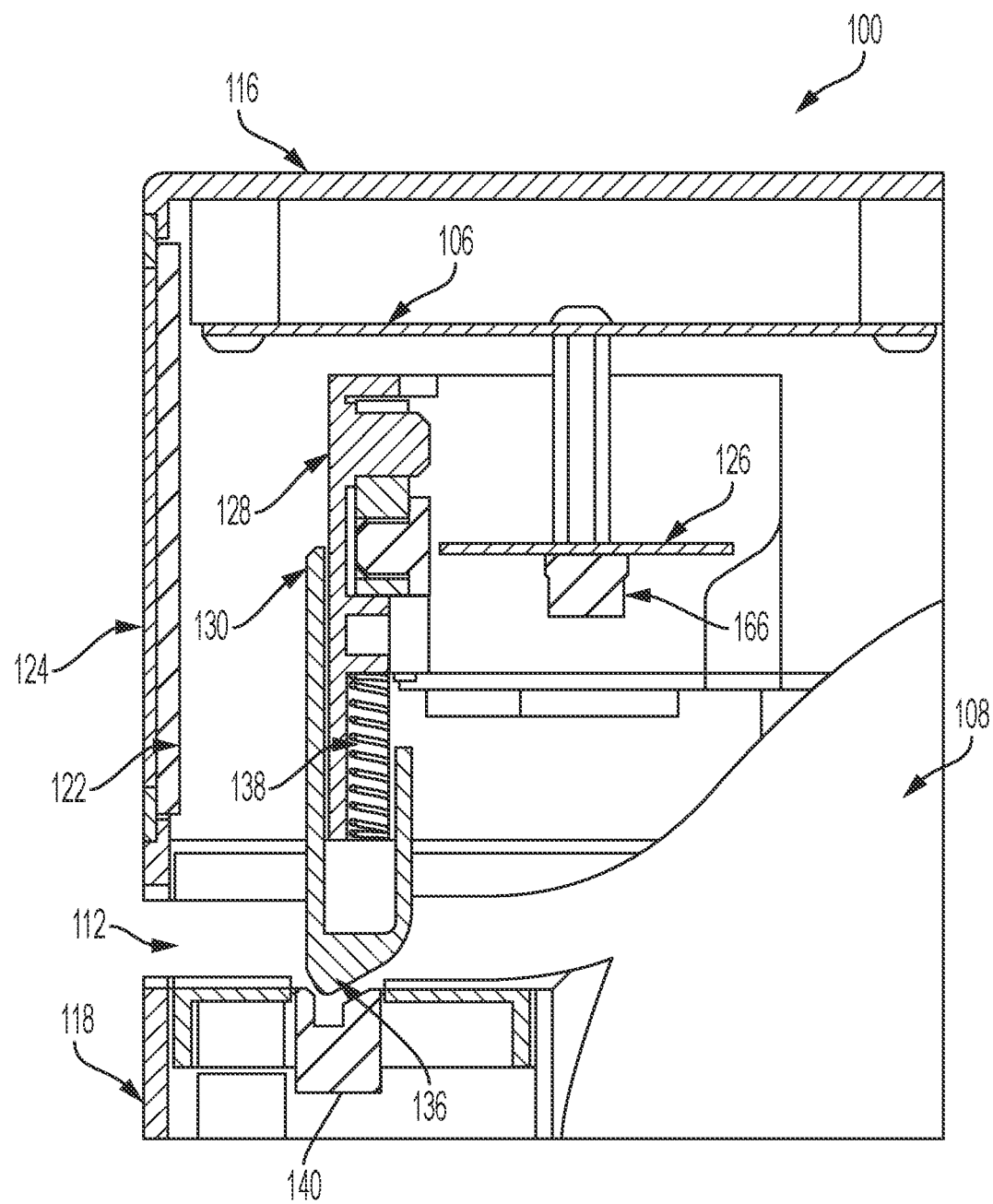
FIG. 6 is a side view of the gate of pill packet dosage tracking device in a closed position in accordance with embodiments of the present invention.
Figure 7:
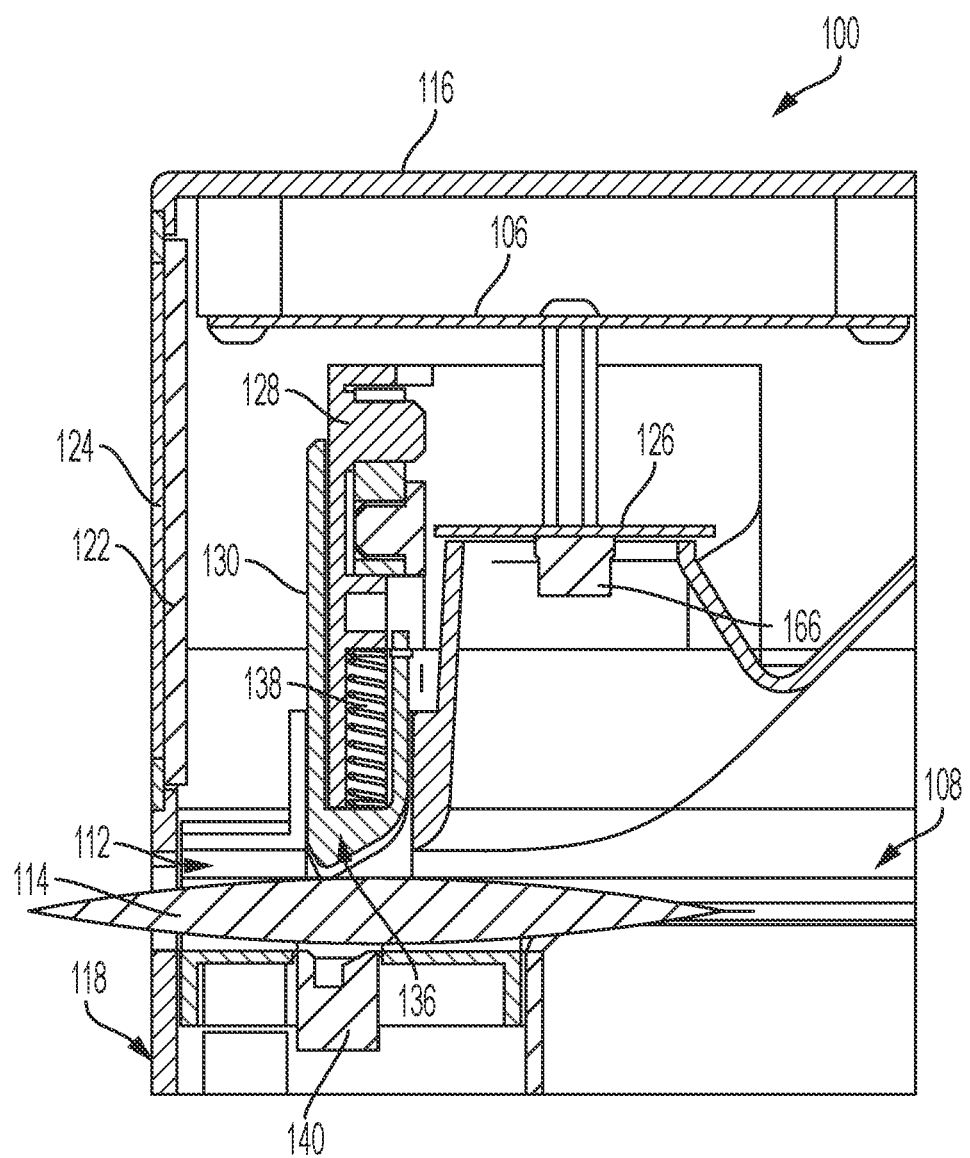
FIG. 7 is a side view of the gate of pill packet dosage tracking device transitioning to an open position around a pill packet in accordance with embodiments of the present invention.
Figure 8:
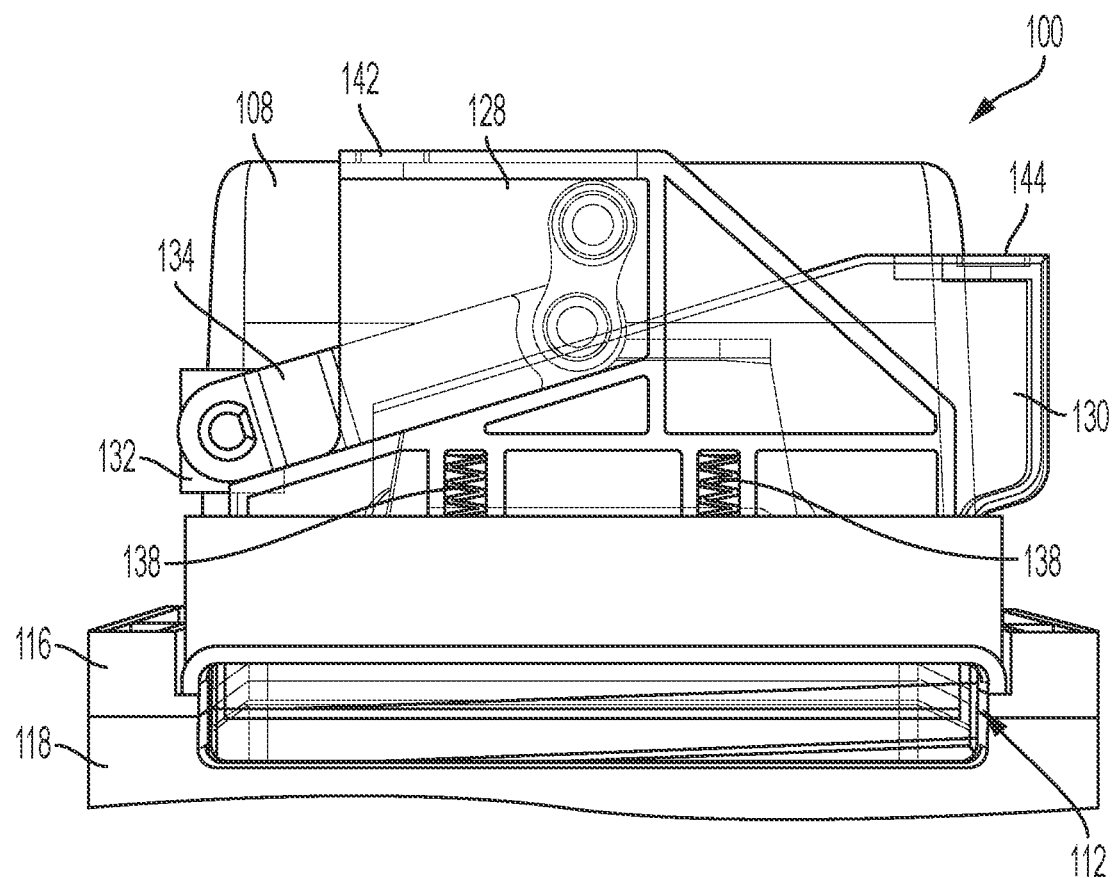
FIG. 8 is a transparent front view of the pill packet dosage tracking device showing the interaction of the elements of the gate in a closed position in accordance with embodiments of the present invention.
Figure 9:
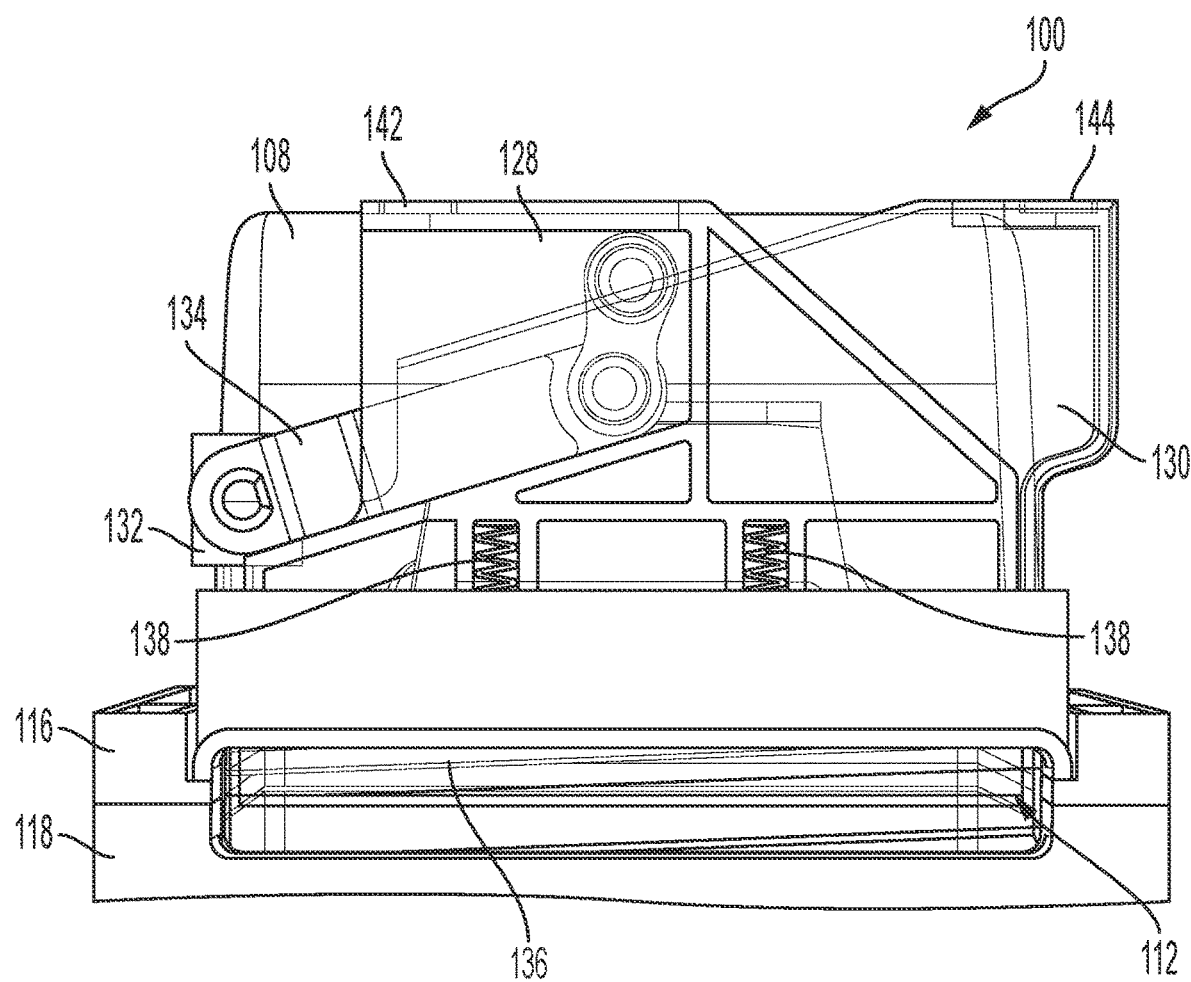
FIG. 9 is a transparent front view of the pill packet dosage tracking device showing the interaction of the elements of the gate in an open position in accordance with embodiments of the present invention.
Figure 10:
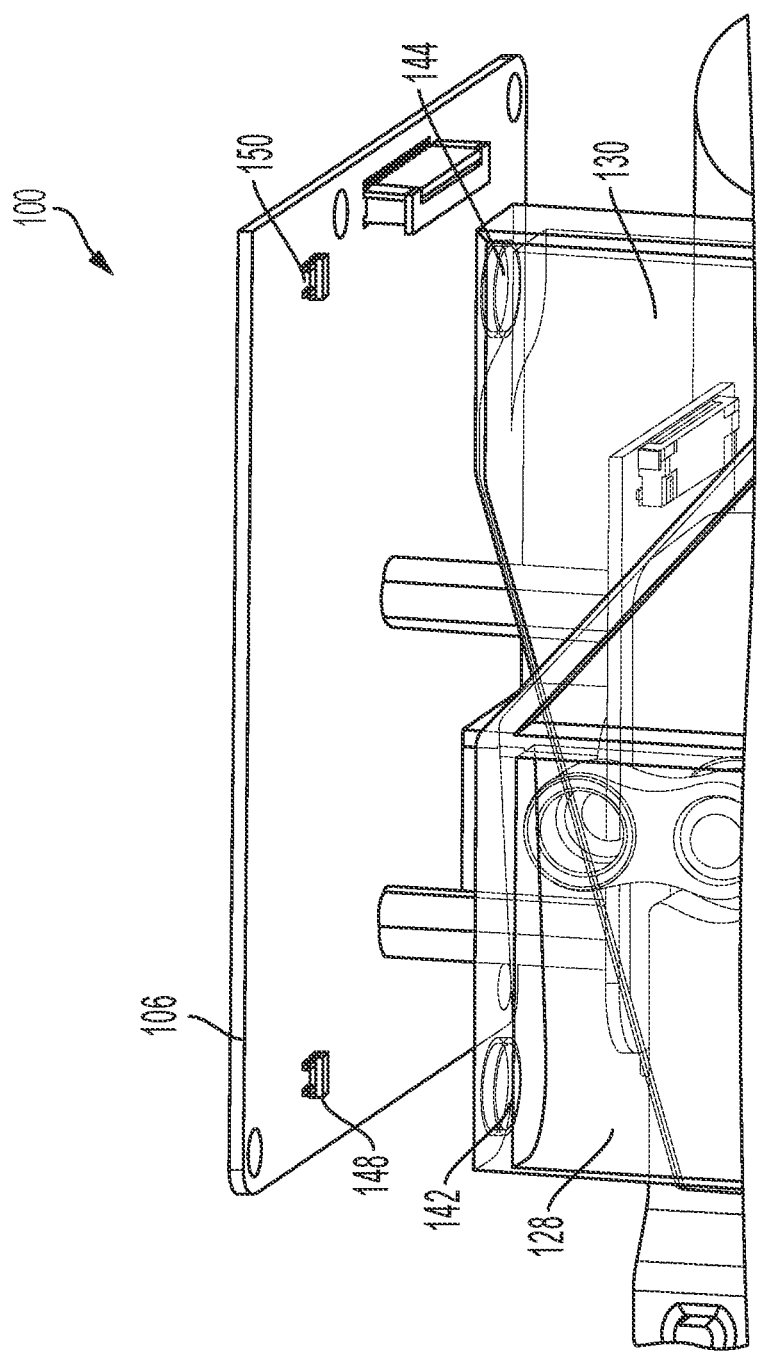
FIG. 10 is a transparent perspective view of the pill packet dosage tracking device showing a sensor used to detect the position of the gate in accordance with embodiments of the present invention.

FIG. 6 through FIG. 10 show the operation of the pill packet dosage tracking device 100. FIG. 6 is an exposed side view of the device 100 showing the gate 104 in a biased closed position. FIG. 7 is an exposed side view of the device 100 showing the gate 104 transitioning to an open position as a packet 114 passes through the gate. FIG. 8 is a front view of the device 100 with parts made transparent to show the interaction of the parts when the gate 104 is halfway in the transition from a biased closed position to an open position. FIG. 9 is a front view of the device 100 with parts made transparent to show the interaction of the parts when the gate 104 has transitioned to a fully an open position. FIG. 10 shows the operation of the Hall-Effect sensors 148, 150 in determining the position of the gate 104.

The gate 104 is typically in a biased closed position as seen in FIG. 6 and FIG. 8. In this state the inner slider 128 has moved linearly vertically to be in close proximity to the controller 106 disposed above the gate 104. As discussed previously, the linear vertical movement of the gate is provided by the motor 132 and linkage 134 and is controlled by the processor 146 of the controller 106. Moving the inner slider 128 to position this allows the outer slider 130 full vertical linear movement in relation to the inner slider 128. Here the springs 138 bias the outer slider 130 away from the inner slider toward the receiver 140, which is configured to receive the engagement edge 136 of the outer slider 130. In some embodiments, the device 100 identifies individual pill packets 114 mechanically by sensing the change in thickness of the pill packet 114 as it passes through the device 100. As a stream of pill packets 110 passes thru the extraction channel 112 and under the gate 104, the contained pill(s) push or otherwise wedge open the gate 104. An example of this can be seen in FIG. 7. FIG. 9 also shows the outer slider 130 halfway in the transition from the closed position to the opened position but without the individual pill packet 114 so as to provide an unobstructed view of the engagement edge 136 of the outer slider 130. In certain embodiments, such as seen in FIG. 6 through FIG. 9, the engagement edge 136 of the outer slider 130 has an asymmetrical shape, such as a guillotine blade shape. This aids in allowing the pill packet 114 to push or wedge the outer slider 130 of the gate 104 vertically linearly up and out of the way as the pill packet 114 is pulled out during extraction. The spring 138 or compliant mechanism returns the outer slider 130 of the gate 104 to a closed position once the pill(s) have passed under.

As seen in FIG. 10, one or more sensors, such as but not limited to an analog Hall-Effect sensors 148, 150, monitor the position of the inner slider 128 and outer slider 130 of the gate 104 over time to determine when a pill packet 114 passes under the gate 104. In the example of FIG. 6 through FIG. 10, magnet 142 of the inner slider 128 is detected by hall-effect sensor 148 on the controller 106 and magnet 144 of the outer slider 130 is detected by hall-effect sensor 150 on the controller.

In some such embodiments, the device 100 can halt the stream of pill packets 110 from being extracted from the device 100 to control dosing. In such cases, the stream of pill packets 110 is held securely between the engagement edge 136 of the outer slider 130 of the gate 104 and receiver 140. As discussed previously, the gate 104 is provided with a motor 132, allowing the gate 104 to be raised and lowered in response to signaling from the processor 146 of the controller 106. As such, braking is controlled by an on-board processor 146 or in some case in response from an external processor, based on knowledge of dose and counting and/or identifying the pill packets 114 as they pass through the gate 104, where pill packets 114 are presented to the user.

In some embodiments, the compliant nature of the gate 104 allows the user to overpower the mechanism of the gate 104 in the case of mechanical, power, electronic, software, or communication failure. This improves patient safety and facilitates regulatory approval of the device 100.

In some embodiments, the device 100 can scan or identify markings printed on the pill packet 114 using a sensor 126, that makes use of an optical scanner such as a photodetector, photodetector array, or camera 166. In some cases, the markings on the pill packet 114 may be human-readable, in which case an optical character recognition (OCR) method implemented by the processor 146 of the controller 106 may be employed. In some cases, the markings maybe designed for computer readability, such as barcodes, QR codes, AprilTags, or other visual fiducial marker. In some cases, these markings may be printed, etched, lasered, or molded. In other cases, these markings may be created by bonding reflective or nonreflective material to the pill packet 114, or material that has otherwise different optical properties from the material of the stream of pill packets 110. The pill packets 114 may also be modified with hole punches or other mechanical features to alter the flow of light through the pill packet 114.

In other embodiments, the device can scan or identify pill packets 114 by automatic optical inspection of the medication contained therein. By packaging medication in clear pouches or packets 114, pharmacies can allow the device 100 to photograph the pill packet 114 using the camera 166 and identify the medication contained therein by consulting a database of known medication images. This visual identification or verification can be used in conjunction with the mechanical tracking of pill packets 114 to further ensure proper dosing.

As discussed previously, in some embodiments, the device can communicate directly with the Internet or other devices using Wi-Fi®, Bluetooth® Ethernet, and/or cellular connectivity, or other wireless communication protocol, to allow remote monitoring of when packets are consumed. An example of such connectivity can be seen in FIG. 11.

Figure 11:
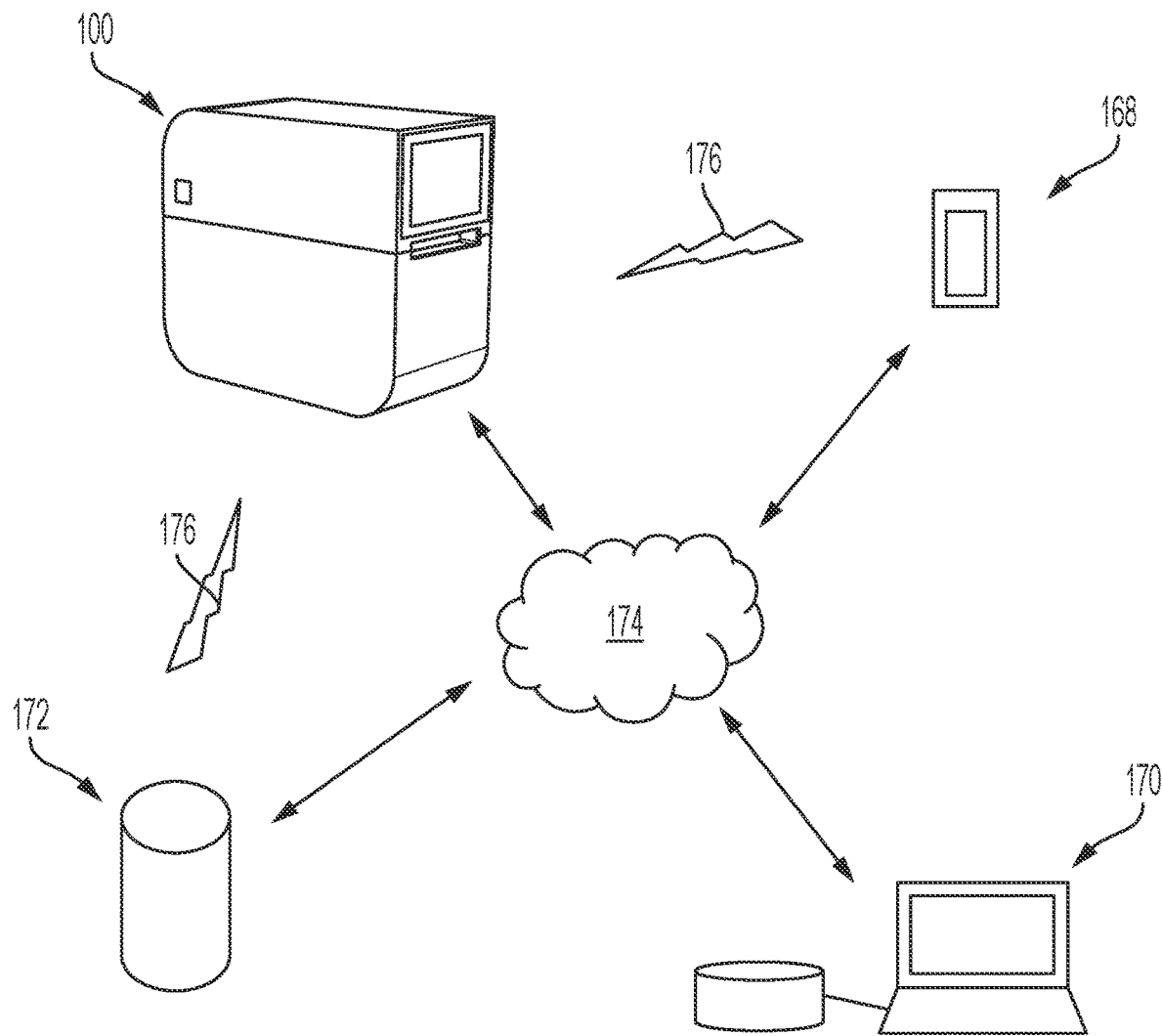
FIG. 11 depicts a communication networks showing the connectivity of the pill packet dosage tracking device in accordance with embodiments of the present invention.

In the exemplary network of FIG. 11, the device 100 may be in communication with one or more devices such as a personal electronic or computing device 168 such as a smart phone, tablet, or personal computer; a remote monitoring system or server 170; and a smart device 172 such as a smart speaker, such as Amazon Echo™ or Google Home™. The communication may be over the internet 174 or through direct device to device communication 176 radio, Bluetooth®, or cellular communication, or the like. The personal electronic or computing device allow a user, either a patient or care-giver, to control and configure the operation of the device 100. Similarly, the device 100 can be controlled by the remote monitoring system or server 170 allowing hospitals, nursing homes, or other care facilities fleet management of the device 100. The remote monitoring system or server 170 may also be used by the device to confirm medications and dosages provided by the pill packets 114. In other embodiments, the personal electronic of computing system 168, remote monitoring system or server 170, or smart device 172 may perform as or part of an authorization mechanism that prevent unauthorized extraction of pill packets 114 from the device 100.

In some embodiments, dosing data are stored internally and retrieved manually, e.g. by copying files to a USB flash drive. This allows monitoring even when Internet access is not available or desired.

In some embodiments, the device 100 has GPS and/or biometric authentication used in concert with dosing data to control the gated mechanism. This prevents the device 100 from releasing medication to people other than the designated patient, or to prevent removal of medication outside the user's home. In some such embodiments, the processor 146 of the device 100 can communicate with the personal electronic or computing device 168, such as smart phone, tablet, digital assistant appliance, or computer, allowing the device 168 act as or part of an authorization mechanism to authenticate users with biometric recognition (e.g., by fingerprint, facial or voice profile) or an ability to transmit its GPS coordinates. In still other embodiments, the smart device 172 may provide some or all of this functionality when acting as an authorization mechanism.

In some embodiments, the display 122 of the device 100 provides a user interface, in some embodiments having touch screens 124, which can display dosing schedules, present medication information, provide visual notifications and reminders, and enable device provisioning, enrollment, and/or initial setup. The device 100 may also contain a microphone and/or speaker for voice interaction. In certain embodiments the display, microphone, and/or speaker may be provided by the personal electronic or computing device 168 or the smart device 172 such as when the devices 168, 172 are acting as or part of an authorization mechanism. The display 122 provides device configuration, user input, and visual feedback. the speaker provides auditory reminders and other feedback. the microphone allows for voice control.

For medications prescribed on an "As Needed" (PRN) basis (e.g., opioids to be taken only with continuing pain at a designated time), a roll containing the controlled medication may be similarly pulled through, only after the patient indicates his need, for example, by pushing a button on the touchscreen interface of the device. The need for such PRN dosing can thus be monitored by the prescriber.

To maintain health and reduce hospitalizations, it is essential that non-adherence be promptly detected, allowing intervention, especially by medically trained associates of the patient's providers. Therefore, the data-based system will promptly notify a designated clinician of non-adherence, so that instructions on omitted or late dosing can be communicated to the patient.

Figure 12:
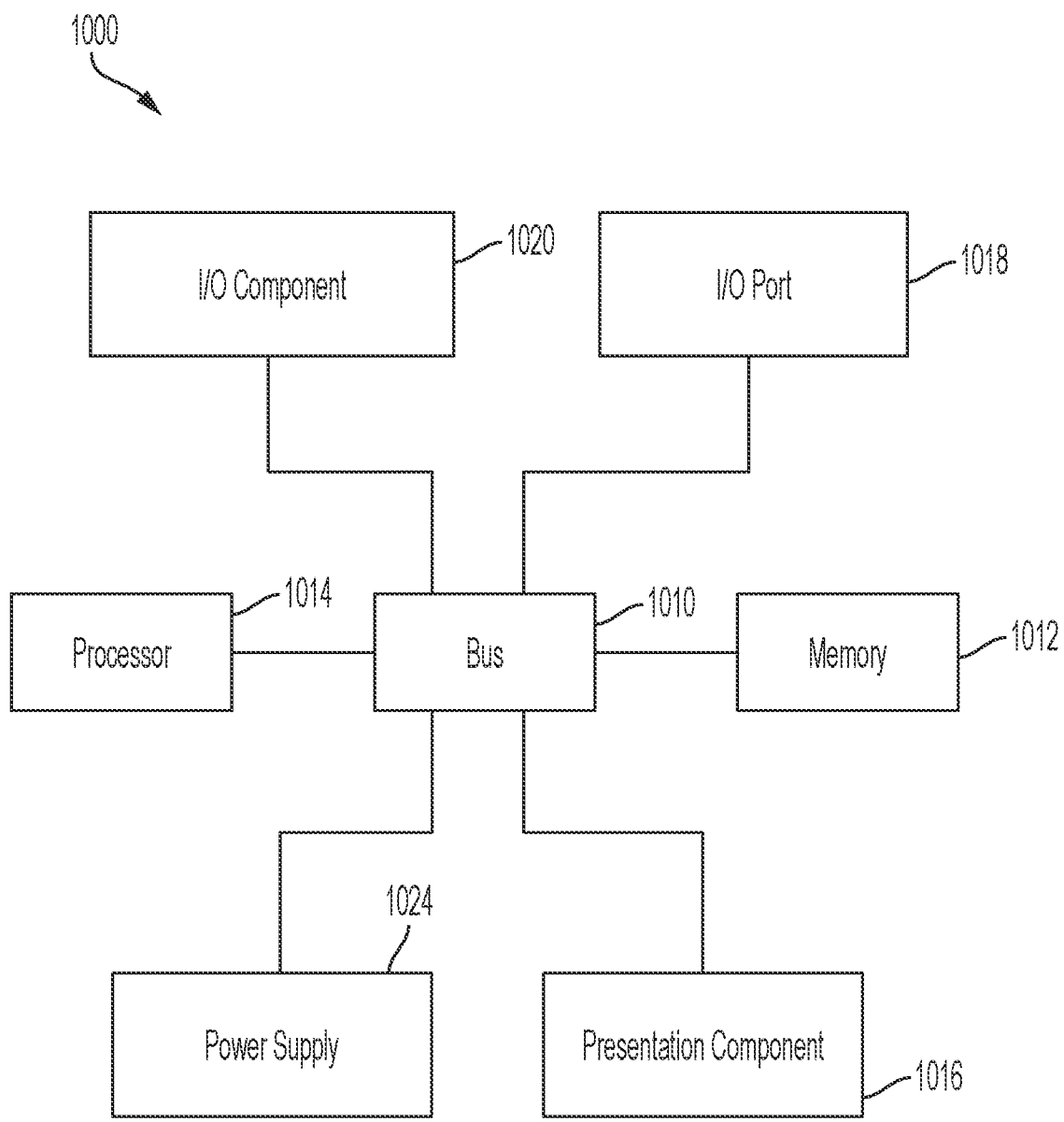
FIG. 12 is a diagrammatic illustration of a computing device and related hardware for use in implementation of the present invention.

FIG. 12 depicts an example electronic, computer, or computing device 1000 that can be used to implement one or more aspects of the present invention, including control of the device 100 or personal electronic or computing device 168, remote monitoring system or server 170 or smart device 172. The functionality and hardware of such computing device 1000 may be implemented in any of the electronic hardware systems or subsystems described herein as involving or using a "computer" or "computing device" or the like, or related hardware for providing all or part of the described functionality, provided as a separate device or integrated into a system or subsystem described herein, as would be appreciated and understood by those of skill in the art. The terms "computer", "computing device", and the like utilized herein are intended to mean a processor at its most basic form, on up to more complex computing systems, including servers and cloud-based systems, in accordance with conventional meanings of such terms. However, for purpose of completeness, example components and related accessories that are intended to be encompassed by the use of the terms "computer", "computing device", "processor", and the like will be provided below in example nonlimiting form.

The computing device 1000 is merely an illustrative example of a suitable computing environment and in no way limits the scope of the present invention. An "electronic device", "remote device," or "personal electronic device" as represented in figures and description herein, can include a "workstation," a "server," a "laptop," a "desktop," a "handheld device," a "mobile device," a "tablet computer," a "processor," or other computing devices, as would be understood by those of skill in the art. Given that the computing device 1000 is depicted for illustrative purposes, embodiments of the present invention may utilize any number of computing devices 1000 in any number of different ways to implement a single embodiment of the present invention. Accordingly, embodiments of the present invention are not limited to a single computing device 1000, as would be appreciated by one with skill in the art, nor are they limited to a single type of implementation or configuration of the example computing device 1000.

The computing device 1000 can include a bus 1010 that can be coupled to one or more of the following illustrative components, directly or indirectly: a memory 1012, one or more processors 1014, one or more presentation components 1016, input/output ports 1018, input/output components 1020, and a power supply 1024. One of skill in the art will appreciate that the bus 1010 can include one or more busses, such as an address bus, a data bus, or any combination thereof. One of skill in the art additionally will appreciate that, depending on the intended applications and uses of a particular embodiment, multiple of these components can be implemented by a single device. Similarly, in some instances, a single component can be implemented by multiple devices. As such, the figures herein are merely illustrative of an exemplary computing device 1000 that can be used to implement one or more embodiments of the present invention, and in no way limits the invention.

The computing device 1000 can include or interact with a variety of computer-readable media. For example, computer-readable media can include Random Access Memory (RAM); Read Only Memory (ROM); Electronically Erasable Programmable Read Only Memory (EEPROM); flash memory or other memory technologies; CDROM, digital versatile disks (DVD) or other optical or holographic media; magnetic cassettes, magnetic tape, magnetic disk storage or other magnetic storage devices that can be used to encode information and can be accessed by the computing device 1000.

The memory 1012 can include computer-storage media in the form of volatile and/or nonvolatile memory. The memory 1012 may be removable, non-removable, or any combination thereof. Exemplary hardware devices are devices such as hard drives, solid-state memory, optical-disc drives, and the like. The computing device 1000 can include one or more processors that read data from components such as the memory 1012, the various I/O components 1020, etc. Presentation component(s) 1016 present data indications to a user or other device. Exemplary presentation components include a display device, speaker, printing component, vibrating component, etc.

The I/O ports 1018 can enable the computing or electronic device 1000 to be logically coupled to other devices, such as I/O components 1020. Some of the I/O components 1020 can be built into the computing device 1000. Examples of such I/O components 1020 include a sensor (including but not limited to: weight sensor, infrared sensor, camera, chemical sensor, microphone, or the like), keypad, touchpad, joystick, recording or storage device, game pad, satellite dish, scanner, printer, wireless device, networking device, and the like, as appropriate.

Since suicidal ideation has been associated with the taking of antidepressants and Anti-Epileptic Drugs, a virtual button on the device 100 (or verbal request to Alexa) can indicate the need for immediate psychiatric assistance for patients on such therapies.

Additional features of the device 100 of the present invention can include improved security. Specifically, devices can have Bluetooth® connectivity to the device 100 sensing a signal that the device is operational (heartbeat). If the device 100 is taken outside a range of the controlling processor, the device locks and the monitoring network is notified. Likewise, the device 100 can notify a monitoring network such as a remote monitoring system or server 170, if the device 100 is stolen, based on GPS coordinates or loss of network connectivity.

Anticipating FDA requirements for risk evaluation and mitigation, in the absence of cellular connectivity, a virtual button on the device 100 can signal by Bluetooth® connection to release an appropriate dose.

To any extent utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about" and "approximately" are intended to cover variations that may existing in the upper and lower limits of the ranges of subjective or objective values, such as variations in properties, parameters, sizes, and dimensions. In one non-limiting example, the terms "about" and "approximately" mean at, or plus 10 percent or less, or minus 10 percent or less. In one non-limiting example, the terms "about" and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A pill packet dosage tracking device, the device comprising:
   a container, comprising:
      a reservoir configured to hold a stream of pill packets; and
      an extraction channel configured to guide passage of the stream of pill packets from the reservoir out of the container;
   a gate, comprising:
      an engagement edge for engaging the stream of pill packets;
      a motor for positioning the gate between a closed position and an open position;
      an inner slider;
      an outer slider slidably coupled to the inner slider and having an engagement edge for engaging the stream of pill packets; and
      a linkage connecting the motor to the inner slider wherein the linkage converts rotational movement of the motor to linear movement of the gate; and
   a controller that monitors the extraction of pill packets and controls transition of the gate between the closed position and the open position by control of the motor;
   wherein the gate is disposed in the extraction channel and vertically transitions between a closed position holding the stream of pill packets in place and an open position allowing advancement and extraction of a pill packet; and
   wherein the advancement and extraction of pill packets occur by a user pulling the pill packets out of the device without requiring a motor to advance the stream of pill packets.

2. The device of claim 1, wherein the stream of pill packets comprises one or more packet of containing a predetermined dosage of pills wherein each pill packet is detachably connected to a next pill packet in the stream.

3. The device of claim 1, wherein the container further comprises an upper shell and a lower shell wherein removing the upper shell provides access to the reservoir and extraction channel.

4. The device of claim 1, wherein the gate is mechanically biased in a closed position by springs between the inner slider and outer slider.

5. The device of claim 1, further comprising a receiver that receives the engagement edge of outer slider when the gate in a closed position.

6. The device of claim 1, wherein the engagement edge of the outer slider has an asymmetrical shape.

7. The device of claim 6, wherein the engagement edge has a guillotine blade configuration.

8. The device of claim 1, wherein extracting a pill packet from the container through the extraction channel causes the gate to transition from a closed position to an open position, indicating to the controller that a pill packet has been extracted.

9. The device of claim 1, wherein the controller maintains a count of pill packets extracted from the device.

10. The device of claim 1, wherein the controller detects the extraction of one or more pill packets corresponding to a timed dosage and locks the gate in a closed position until a next timed dosage.

11. The device of claim 1, wherein the controller comprises:
   a processor that monitors the extraction of pill packets; and
   one or more sensors that detect the position of the gate.

12. The device of claim 1, wherein the controller further comprises wireless connectivity.

13. The device of claim 12, wherein the device can be controlled remotely.

14. The device of claim 1, further comprising a display mounted on the container providing a status of the device.

15. The device of claim 14, wherein the display comprises a touch screen display.

16. The device of claim 1, further comprising a sensor disposed along the extraction channel configured to detect a pill packet.

17. The device of claim 16, wherein the sensor comprises an optical scanner.

18. The device of claim 16 wherein the sensor comprises a camera.

19. The device of claim 1, further comprising an authorization mechanism in communication with the controller.

* * * * *